United States Patent [19]

Konrad et al.

[11] 4,107,218

[45] Aug. 15, 1978

[54] DECOLORATION OF BISPHENOL-A RECYCLE STREAM WITH CATION EXCHANGE RESIN

[75] Inventors: Frederick Miller Konrad, Basking Ridge, N.J.; Stephen Howard Mason, Ponce, P.R.

[73] Assignee: Union Carbide Corporation, New York, N.Y.

[21] Appl. No.: 794,419

[22] Filed: May 6, 1977

Related U.S. Application Data

[63] Continuation-in-part of Ser. No. 696,726, Jun. 16, 1976, abandoned, which is a continuation-in-part of Ser. No. 616,026, Sep. 23, 1975, abandoned.

[51] Int. Cl.$^2$ ............................................. C07C 37/22
[52] U.S. Cl. .................................................... 560/724
[58] Field of Search ........... 260/619 A, 619 R, 621 A

[56] References Cited

U.S. PATENT DOCUMENTS

| | | | |
|---|---|---|---|
| 2,861,948 | 11/1958 | McKellar | 260/621 A |
| 2,911,363 | 11/1959 | Kissling | 260/621 A |
| 3,049,568 | 8/1962 | Apel et al. | 260/619 A |
| 3,049,569 | 8/1962 | Apel et al. | 260/619 A |
| 3,221,061 | 11/1965 | Grover et al. | 260/619 A |
| 3,896,006 | 7/1975 | Cooke | 260/621 A |

OTHER PUBLICATIONS

Soviet Plastics #8, 27 (1970)—"Preparation of Bisphenol With a Spirocyclic Structure Using Cation Exchange Resins", Kutsenko et al.

*Primary Examiner*—Edward M. Woodberry
*Attorney, Agent, or Firm*—Franklyn Schoenberg

[57] ABSTRACT

All or part of bisphenol-A process mother liquor recycle stream is contacted with acidic cation exchange resin to remove color bodies. The acidic cation exchange resin is periodically washed and reactivated after use by a mixed phenol/water wash.

4 Claims, 1 Drawing Figure

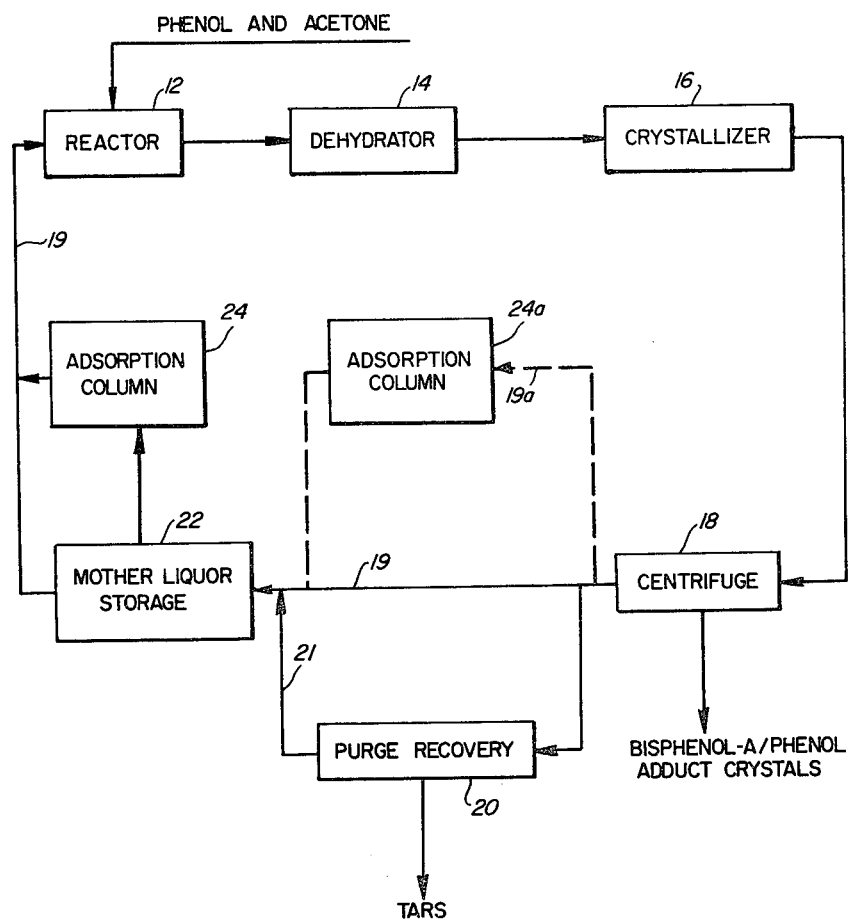

DECOLORATION OF BISPHENOL-A RECYCLE STREAM WITH CATION EXCHANGE RESIN

This application is a continuation-in-part of application Ser. No. 696,726 filed June 16, 1976, now abandoned which was a continuation-in-part of application Ser. No. 616,026 filed Sept. 23, 1975, now abandoned.

The invention relates to a process for reducing the content of color bodies in 4,4'-bisphenol-A recycle stream by contacting all or part of the bisphenol-A process mother liquor recycle stream with an acidic cation exchange resin which is periodically reactivated by washing with a phenol/water mixture.

2,2-Bis(4-hydroxyphenyl)propane ("4,4'-bisphenol-A") is produced by reacting a stoichiometric excess of phenol with acetone in the presence of an acidic cationic exchange resin catalyst, see Farnham et al., U.S. Pat. No. 3,242,219, and also in the presence of a bound mercaptan reaction promoter, see F. N. Apel et al., U.S. Pat. No. 3,049,568, Wagner, U.S. Pat. No. 3,172,916, McNutt et al., U.S. Pat. No. 3,394,089, and Gammill et al., U.S. Pat. No. 3,634,341. A preferred process employs an acidic cationic exchange catalyst including the use of a soluble mercaptan promoter, see Farnham et al., Canadian Pat. No. 859,204. The effluent from the phenol/acetone reaction contains unreacted starting materials, soluble promoter, if employed, 4,4'-bisphenol-A, water, and by-products. After removal of volatile materials (e.g., acetone, water, volatile promoter, if employed, and some phenol), the effluent is cooled to about 40°–50° C. to form a crystalline 1:1 (molar) adduct of phenol and 4,4'-bisphenol-A. The crystalline adduct is then separated from the mother liquor and is processed further to remove the phenol and recover substantially pure 4,4'-bisphenol-A. After separation from the adduct, the mother liquor is recycled. The mother liquor contains about 80 weight percent phenol, plus 4,4'-bisphenol-A and impurities.

The principal component of the impurities is 2,4'-bisphenol-A. if 2,4'-bisphenol-A were the only impurity, all of the mother liquor could be recycled, because for example, as disclosed in Grover et al., U.S. Pat. No. 3,221,061, the principal reaction of phenol with acetone forms an equilibrium mixture of the 4,4'- and 2,4'-isomers. There would then be no net loss of raw material to by-products. However, a small but significant proportion of other by-products is also formed. These other by-products include trisphenols, higher polyphenols, Dianin's compound, and a very small proportion of highly colored compounds characterized by intense absorption of ultraviolet light. If all of the mother liquor were recycled as disclosed, for example, in U.S. Pat. No. 3,221,061, the concentration of these materials (especially the highly colored compounds) in the process stream would gradually build up to an unacceptable level. In some processes, therefore, a portion of the mother liquor is continuously drawn off or purged. The purged mother liquor is subjected to evaporation to recover most of the phenol contained therein, and the remaining material is discarded. This represents a raw material loss of the order of 0.1 pound per pound of product.

An improvement wherein much of the purged mother liquor can be reclaimed is described in Frevdewald, British Pat. No. 1,340,869. In accordance with Freudewald's process, the purged mother liquor is subjected to elevated temperature in the presence of an alkaline catalyst. Much of the bisphenols and other impurities in the mother liquor are thereby cleaved to form phenol and para-isopropenyl-phenol ("IPP"), with only a small amount of unusable residue being formed. The phenol and IPP cleavage products (including IPP dimer) are processed in a reactor wherein the phenol and IPP or IPP dimer combine in the presence of acid catalyst to form 4,4'-bisphenol-A. This stream is recombined with the mother liquor recycle stream. Therefore, in accordance with Freudewald's improvement, some of the residue from the purged mother liquor that had theretofore been discarded, is recovered. The raw material loss is reduced to the order of 0.05 pound per pound of product.

It is characteristic of both of the above-described modes of operating the bisphenol-A process that a certain percentage of the raw materials must be discarded in order to avoid build-up of highly colored compounds or color bodies. This is true regardless of the grade of 4,4'-bisphenol-A being produced. Thus, while epoxy resin grade 4,4'-bisphenol-A can tolerate higher proportions of the 2,4'-isomer, trisphenols, etc., than polycarbonate grade, color bodies are undesirable in both. Therfore, even though the amount of color bodies in the process stream is quite small, an unavoidable loss of raw material in an amount much greater than the proportion of color bodies, must be incurred in order to prevent the production of a discolored product. Obviously, a means for selectively removing the color bodies from the 4,4'-bisphenol-A process stream would be desirable as a means for reducing the loss of raw material.

In accordance with the present invention, a process is provided for reducing the content of color bodies in 4,4'-bisphenol-A process recycle stream, wherein a stoichiometric excess of phenol is reacted with acetone in a reaction mixture containing an acid catalyst and preferably a mercaptan reaction promoter, to produce a product mixture containing phenol and 4,4'-bisphenol-A, wherein said product mixture is separated into a 4,4'-bisphenol-A/phenol adduct and a mother liquor recycle stream, and wherein said mother liquor recycle stream is recycled to said reaction mixture; which process comprises contacting at least a portion of said mother liquor recycle stream with a substantially insoluble acidic cationic exchange resin for a period of time and at a temperature sufficient to reduce the content of color bodies contained in said mother liquor recycle stream, prior to recycling said mother liquor to said reaction mixture. The acidic cation exchange resin is periodically reactivated by washing with a phenol/water mixture.

An understanding of the invention will be apparent from the following detailed description and the accompanying drawings, in which the sole FIGURE is a schematic flow diagram illustrating two embodiments of the invention.

Referring now to the drawing, a stoichiometric excess of phenol, acetone, and a mercaptan reaction promoter such as ethyl mercaptan, are fed to a reactor 12 that is maintained at a temperature of, for instance 55°–80° C, and which contains an acid catalyst such as sulfonated styrene-divinylbenzene ion exchange resin. Alternatively, a mercaptan reaction promoter can be combined with an acid catalyst such as sulfonated styrene-divinylbenzene ion exchange resin in the reactor as disclosed, for example, in McNutt et al., U.S. Pat. No. 3,394,089 and Gammill et al., U.S. Pat. No. 3,634,341 and addition thereof with the phenol and acetone feed can be eliminated. In the reactor 12, the reaction of phenol with acetone to produce 4,4'-bisphenol-A occurs. The product stream flowing from the reactor 12 contains phenol, 4,4'-bisphenol-A, some unreacted acetone, mercaptan promoter, water, and by-products. The product stream flows from the reactor 12 to a dehydrator 14, in which the acetone, mercaptan promoter, water, and some of the phenol are stripped from the product stream. The dehydrated product stream flows from the dehydrator 14 to a crystallizer 16, in which 4,4'-bisphenol-A/phenol adduct crystals are precipitated by cooling. The slurry of mother liquor and adduct crystals flows from the crystallizer to a solid-liquid separator such as a centrifuge 18, in which the mother liquor and adduct crystals are separated. The 4,4'-bisphenol-A product is recovered from the adduct crystals by known techniques (not shown). The mother liquor flows from the centrifuge 18 to a mother liquor storage container 22, prior to being recycled to the reactor 12. At least a portion of the mother liquor flowing from the centrifuge 18 may be introduced into a purge recovery reactor 20, in which it is subjected to elevated temperature (e.g., 100° to 300° C., and preferably 150° to 250° C.) in the presence of a base catalyst, to cleave the bisphenols and other polyphenols present in the mother liquor to phenol and IPP, including IPP dimer. The phenol and IPP products of the cleavage reaction are continuously removed from the purge recovery reactor 20, as by distillation, and the cleavage reaction product stream 21 is returned to the mother liquor recycle stream 19.

Before being recycled to the reactor 12, at least a portion of the mother liquor recycle stream 19 flows from the mother liquor storage container 22 to an adsorption column 24, in which it is contacted with an acidic cation exchange resin, under conditions that will be more fully described below. In the adsorption column 24, color bodies that are present in the mother liquor recycle stream 19 are removed. In the FIGURE, the adsorption column 24 is located in the flow stream between the mother liquor storage 22 and the reactor 12. Alternatively, an adsorption column 24a can be located between the centrifuge 18 and the mother liquor storage 22, where it can receive all or some of that portion of the mother liquor recycle stream 19a that did not pass through the purge recovery reactor 20. In some cases, as when making epoxy resin grade 4,4-bisphenol-A, the purge recovery reactor 20 can be by-passed altogether.

The acidic cation exchange resin employed in the invention is a macroreticular cation exchange resin in the acid form. For instance, sulphonated divinylbenzene-styrene copolymers are illustrative of useful ion exchange resins. The ion exchange resin should be substantially anhydrous. That is, the water content of the ion exchange resin should be in equilibrium with the water content of the mother liquor. Thus, when the water content of the mother liquor is about 2 weight percent, the ion exchange resin should contain not more than about 5 to 10 weight percent water.

The temperature in the adsorption column is not narrowly critical. Temperatures within the range of from about 40° to about 150° C., and preferably from about 40° to about 80° C., are usually employed. At temperatures below about 40° C., the phenol in the mother liquor may freeze, and at temperatures above about 150° C., the ion exchange resin may become unstable.

The throughput rate of the mother liquor recycle stream through the adsorption column is also not narrowly critical. For instance, the throughput rate can be up to about 15 ion exchange resin bed volumes per hour. The preferred throughput rate is from about 1 to about 3 bed volumes per hour.

The adsorbed color bodies can be desorbed from the acidic cation exchange resin bed by a phenol/water wash. The phenol/water wash can contain from about 2 to about 70, and preferably from about 20 to about 50, weight percent water. Distillation can be used to reclaim the phenol/water wash by removing the color bodies therefrom.

In the Examples below, the content of color bodies in the mother liquor recycle stream was measured as the absorbance of an ultraviolet wave length of 350 nm (microns). The procedure used for measuring the absorbance was the following:

1. PURPOSE
   1a — This method is used to obtain an adsorbance at 350 nm of bisphenol-A process samples.
2. APPARATUS
   2a — UV Spectrophotometer (Bausch and Lomb Spectronic 505, or equivalent), capable of being used with 10-centimeter cells.
   2b — A matched pair of cylindrical silica cells with 10.0 centimeter path length.
   2c — Analytical balance.
   2d — Erlenmeyer flasks, glass stoppered, 250 milliliters.
3. REAGENTS
   3a — Methanol, reagent grade, suitable for spectrophotometry.
4. PROCEDURE
   4a — The weight of sample used for the determination is dependent on the source of the sample. A 1.00 ± 1.01 gram sample is used for samples from the reaction system, dehydrator, crystallizer, mother liquor recycle stream, or purge plant. A 10.0 ± 0.1 gram sample is used for samples from anywhere in the process after the crystallizer through to final product.
   4b — Using an analytical balance, add the appropriate weight (see 4a) of process sample to a 250 milliliter Erlenmeyer flask. To 1 gram samples, add 110 milliliters of methanol; to 10 gram samples 110 milliliters of methanol: Mix thoroughly.
   4c — Fill two clean 10.0-centimeter matched silica cells with methanol and place them in the sample and reference beams of the spectrophotometer.
   4d — Set the wavelength of the spectrophotometer to 350 nm and, after waiting 2 minutes for equilibration, zero the instrument.
   4e — Remove the cell from the sample compartment of the spectrophotometer and discard the methanol.
   4f — Fill the cell with sample solution and place back into the sample compartment of the spectrophotometer.
   4g — Allow 2 minutes for equilibration, then measure the absorbance of the sample solution at 350 nm versus methanol as reference either by recording at the fixed wavelength or by scanning from 320–360 nm.
   4h — Remove the sample cell, discard the solution, and clean the cell thoroughly. Fill the cell once again with methanol and recheck the instrument zero at 350 nm. If original zero setting is maintained use absorbance value recorded in 4g. If zero has changed, repeat the measurement beginning with 4e.

5. CALCULATIONS

4a $$A^* = (A_s\, 33\, 10)/S.W.$$

where:

$A^*$ = an absorbance calculated on the basis of a concentration of 10 grams of sample in 100 milliliters of methanol.

$A_s$ = observed absorbance of the methanolic solution of the sample at 350 nm.

$S.W.$ = sample weight in grams

6. REPORT

6a — Report A* as the absorbance of the sample.

The Examples which follow illustrate the invention. (All percentages are by weight, unless otherwise specified.)

EXAMPLE 1

A 25 millimeter diameter glass column was charged with 210 milliliters of phenol-swollen, macroporous, sulfonated styrene-divinylbenzene ion-exchange resin beads of 10–50 mesh size. The column was jacketed for heating with tempered water. The resin was washed with a solution of 20 weight percent water dissolved in pure phenol. A total of 16 column volumes of wash solvent were pumped through the hydraulically full resin bed downflow at 70 grams/hour and 70° C. The last effluent had an absorbance of 0.5 at 350 nm. measured on a solution of 10 grams effluent diluted with 100 milliliters of methanol in a 10 centimeter cell.

After washing, the resin column was made anhydrous by purging with 10 column volumes of anhydrous phenol at 70 grams/hour and 70° C.

An anhydrous mother liquor (taken from the centrifuge filtrate) which originated from the cation-exchange resin catalyzed condensation of phenol and acetone was used to test the adsorptive capacity of the washed ion-exchange resin described above. This mother liquor had an absorbance of 5.0 and the following composition: 84 percent phenol, 10 percent 4,4'-bisphenol-A, and 6 percent impurities.

Sixty column volumes of mother liquor were pumped downflow through the ion-exchange resin at 80 grams/hour and 70° C. An overall absorbance reduction of 30 percent was obtained as shown in Table I.

TABLE I

| REDUCTION IN 350 ABSORBANCE OF BISPHENOL-A MOTHER LIQUOR BY ION-EXCHANGE RESIN TREATMENT | |
|---|---|
| | Absorbance, 10 grams Diluted With 100 ml. Methanol in 10 cm. Cell At 350 nm. |
| Feed | 5.0 |
| Initial Effluent | 2.0 |
| Final Effluent | 4.5 |
| Composite of Total Effluent | 3.5 |

The loaded ion-exchange resin was washed under the same conditions described above with 8 column volumes of wet phenol (20 percent water) to desorb the chromphoric impurities. The absorbance of the total wash effluent was equivalent to 18.0 on the basis described above.

EXAMPLE 2

100 Grams of the anhydrous (15% water by Karl Fisher) acidic cation exchange resin described in Example 1 was charged to a 1-inch diameter glass column. The resin was washed with 1000 grams of phenol (80%)/water (20%) mixture at 70° C. at 600 grams/hour. The resin was then dried by passing 2000 grams of anhydrous phenol (0.1% H$_2$O) through the bed at 600 grams/hour. Sixty bed volumes (210 milliliters/bed volume) of 4,4'-bisphenol-A process mother liquor having an absorbance of 2.5 were treated by passing it downflow through the bed at a rate of 600 milliliters per hour. The initial effluent had an absorbance of 1.3 — final effluent 2.0. Absorbance of total effluent 1.6 or a reduction of 36%.

Table II shows the rate that the absorptivity of the acidic cation exchange resin depreciates as the feed is pased through the adsorption bed:

TABLE II

| ADSORPTION OF COLOR WITH ADSORBENT | | | |
|---|---|---|---|
| Cumulative Feed (ml) | Absorbance of Feed (350 nm) | Absorbance of Effluent (350 nm) | ΔA |
| 620 | 2.5 | 1.3 | 1.2 |
| 3100 | " | 1.3 | 1.2 |
| 5580 | " | 1.6 | 0.9 |
| 8060 | " | 1.6 | 0.9 |
| 10540 | " | 1.7 | 0.8 |
| 13020 | " | 2.0 | 0.5 |

The resin was washed with 1000 grams of phenol (80%)/water (20%) mixture passed downflow through the bed at 600 grams/hour. The bed was then dried by passing 1000 grams of anhydrous phenol down flow through the bed at 600 grams/hour. Thirty-one bed volumes of regular 4,4'-bisphenol-A process mother liquor with an absorbance of 2.7 was treated by passing it downflow at 600 grams/hour. Absorbance of initial effluent was 1.5 — final effluent 2.0 — Total effluent 1.6 for a reduction of 41%.

Table III shows the results of the second adsorption run after the cation-exchange resin was regenerated as described above. A comparison of Table III with Table II indicated that the ion-exchange resin adsorptive capacity was completely restored by the regeneration step.

TABLE III

| ADSORPTION OF COLOR WITH REGENERATED ADSORBENT | | | |
|---|---|---|---|
| Cumulative Feed (ml) | Absorbance of Feed (350 nm) | Absorbance of Effluent (350 nm) | ΔA |
| 600 | 2.7 | 1.5 | 1.2 |
| 1200 | " | 1.4 | 1.3 |
| 3000 | " | 1.5 | 1.2 |
| 3600 | " | 1.5 | 1.2 |
| 4800 | " | 1.7 | 1.0 |
| 6000 | " | 1.8 | 0.9 |
| 6600 | " | 2.0 | 0.7 |

EXAMPLE 3

In this experiment, several one-gram samples of the acidic cation exchange resin described in Example 1 were saturated with color-bearing impurities. Each sample was then soaked in four grams of solvent at 70° C. for 20 hours. The ratio of phenol to water was varied over a wide range as shown in the table below. Immediately after soaking the solvent was decanted from the resins and its absorbance in the U.V. and visible light region was measured by the procedure described above. The data indicate maximum color desorption when 20–30% by weight of water is in the solvent.

TABLE IV

DESORPTION OF 1 GRAM RESIN WITH 4 GRAMS SOLVENT

| Batch No. | Phenol (wt. %) | Water (wt. %) | Absorbance at 350 nm | Absorbance at 470 nm |
|---|---|---|---|---|
| 1 | 100 | — | 5.4 | .65 |
| 2 | 99 | 1 | 7.7 | .90 |
| 3 | 98 | 2 | 7.6 | .92 |
| 4 | 96 | 4 | 8.4 | 1.2 |
| 5 | 92 | 8 | 10.7 | 1.7 |
| 6 | 84 | 16 | 15.8 | 4.1 |
| 7 | 78 | 22 | 22.8 | 10.1 |
| 8 | 70 | 30 | 26.9 | 7.6 |
| 9 | 68 | 32 | 20.5 | 6.5 |
| 10 | 32 | 64 | 15.0 | 4.4 |

After decantation and prior to measurement of absorbance the solvent from batch 10 was allowed to cool to 25° C. It separated into two liquid layers — an upper aqueous layer containing 10% phenol, and a lower layer containing 70% phenol. The upper aqueous layer was clear and colorless whereas the lower layer was a deep red-brown color. This indicated that the solubility of color bearing impurities in water is low.

The temperature at which the resin bed is washed with the phenol/water mixture is not narrowly critical. As a practical matter, the temperature would not normally be above the boiling point of water. It would be undesirable to carry out the wash above about 120° C. because desulfonation of the resin could occur. The minimum temperature would be the freezing point of the mixture.

Similarly, the quantity of the phenol/water mixture needed is not narrowly critical. The minimim amount needed is of the order of 1 to 1½ adsorbent bed volumes. The maximum is dictated by economics, and other similar factors.

The contact time with the wash is also not critical. Ordinarily, a minimum contact time of about 1 hour will be used, although longer contact times can be used, if desired.

What is claimed is:

1. A process for removing color bodies from 4,4'-bisphenol-A process recycle stream wherein a stoichiometric excess of phenol is reacted with acetone in a reaction mixture containing an acid catalyst to produce a product mixture containing phenol and 4,4'-bisphenol-A, wherein said product mixture is separated into a 4,4'-bisphenol-A/phenol adduct and a mother liquor recycle stream, wherein said mother liquor recycle stream is recycled to said reaction mixture, wherein at least a portion of said mother liquor recycle stream is contacted with an adsorbent comprising a substantially insoluble acidic cationic exchange resin for a period of time and at a temperature sufficient to reduce the content of color bodies contained in said mother liquor recycle stream, said temperature being within the range of from about 40° to about 150° C., prior to recycling said mother liquor to said reaction mixture, wherein said absorbent is periodically washed with a phenol/water mixture to remove absorbed color bodies therefrom, and wherein the water content of said absorbent is substantially in equilibrium with the water content of said mother liquor recycle stream.

2. The process of claim 1 wherein the phenol/water mixture contains from about 2 to about 70 weight percent water.

3. The process of claim 1 wherein the phenol/water mixture contains from about 20 to about 50 weight percent water.

4. The process of claim 1 wherein the phenol/water mixture contains from about 20 to about 30 weight percent water.

* * * * *

UNITED STATES PATENT AND TRADEMARK OFFICE
CERTIFICATE OF CORRECTION

PATENT NO. : 4,107,218
DATED : August 15, 1978
INVENTOR(S) : Frederick Miller Konrad et al.

It is certified that error appears in the above-identified patent and that said Letters Patent are hereby corrected as shown below:

Column 1, line 40, after "phenol-A." delete "if" and insert therefor -- If --

Column 1, lines 64-65, delete "Frevdewald" bridging lines 64 and 65 and insert therefor -- Freudewald --

Column 5, line 7, delete formula "$A^* = (A_S 33\ 10)/S.W.$" and insert therefor -- $A^* = (A_S \times 10)/S.W.$ --

Signed and Sealed this

Tenth Day of July 1979

[SEAL]

Attest:

Attesting Officer

LUTRELLE F. PARKER
*Acting Commissioner of Patents and Trademarks*